(12) United States Patent
Sriwongjanya et al.

(10) Patent No.: US 7,314,640 B2
(45) Date of Patent: Jan. 1, 2008

(54) FORMULATION AND PROCESS FOR DRUG LOADED CORES

(76) Inventors: Mongkol Sriwongjanya, 4163 SW. 67th Ave., #206, Davie, FL (US) 33314; Samuel Yuk, 321 Olivewood Pl., Boca Raton, FL (US) 33431; Avinash Nangia, 1052 Waterside Cir., Weston, FL (US) 33327

(*) Notice: Subject to any disclaimer, the term of this patent is extended or adjusted under 35 U.S.C. 154(b) by 726 days.

(21) Appl. No.: 10/617,456

(22) Filed: Jul. 11, 2003

(65) Prior Publication Data

US 2005/0008701 A1 Jan. 13, 2005

(51) Int. Cl.
- *A61K 9/14* (2006.01)
- *A61K 9/16* (2006.01)
- *A61K 9/48* (2006.01)
- *A61K 9/20* (2006.01)
- *A61K 9/22* (2006.01)

(52) U.S. Cl. .............. 424/490; 424/451; 424/457; 424/458; 424/464; 424/468; 424/469; 424/489; 424/491; 424/493; 424/494

(58) Field of Classification Search .......... None
See application file for complete search history.

(56) References Cited

U.S. PATENT DOCUMENTS

| | | | |
|---|---|---|---|
| 4,281,654 A | 8/1981 | Shell et al. | |
| 4,303,637 A | 12/1981 | Shell et al. | |
| 4,780,318 A | 10/1988 | Appelgren et al. | |
| 4,792,452 A | 12/1988 | Howard et al. | |
| 4,874,613 A | 10/1989 | Hsiao | |
| 4,892,739 A | 1/1990 | Shah et al. | |
| 4,911,707 A | 3/1990 | Heiber et al. | |
| 4,917,676 A | 4/1990 | Heiber et al. | |
| 4,927,640 A | 5/1990 | Dahlinder et al. | |
| 4,942,040 A | 7/1990 | Ragnarsson et al. | |
| 4,952,402 A | 8/1990 | Sparks et al. | |
| 4,957,745 A | 9/1990 | Jonsson et al. | |
| 4,996,047 A | 2/1991 | Kelleher et al. | |
| 5,001,161 A | 3/1991 | Appelgren et al. | |
| 5,019,302 A | 5/1991 | Sparks et al. | |
| 5,081,154 A | 1/1992 | Appelgren et al. | |
| 5,169,638 A | 12/1992 | Dennis et al. | |
| 5,246,714 A | 9/1993 | Dahlinder et al. | |
| 5,288,503 A | 2/1994 | Wood et al. | |
| 5,391,377 A | 2/1995 | Barnwell | |
| 5,399,358 A | 3/1995 | Baichwal et al. | |
| 5,399,362 A | 3/1995 | Baichwal et al. | |
| 5,516,531 A | 5/1996 | Makino et al. | |
| 5,518,730 A | 5/1996 | Fuisz | |
| 5,681,584 A | 10/1997 | Savastano et al. | |
| 5,700,410 A | 12/1997 | Nakamichi et al. | |
| 5,707,656 A | 1/1998 | Lindstedt et al. | |
| 5,785,976 A | 7/1998 | Westesen et al. | |
| 6,022,562 A | 2/2000 | Autant et al. | |
| 6,190,692 B1 * | 2/2001 | Busetti et al. | 424/451 |
| 6,210,712 B1 | 4/2001 | Edgren et al. | |
| 6,284,271 B1 | 9/2001 | Lundberg et al. | |
| 6,287,599 B1 | 9/2001 | Burnside et al. | |
| 6,297,240 B1 | 10/2001 | Embleton | |
| 6,365,185 B1 | 4/2002 | Ritschel et al. | |
| 6,372,254 B1 | 4/2002 | Ting et al. | |
| 6,383,471 B1 | 5/2002 | Chen et al. | |
| 6,491,950 B1 | 12/2002 | Gutierrez-Rocca et al. | |
| 6,569,463 B2 * | 5/2003 | Patel et al. | 424/497 |
| 6,733,789 B1 * | 5/2004 | Stark et al. | 424/490 |
| 7,022,342 B2 * | 4/2006 | Chen et al. | 424/480 |
| 2004/0142035 A1 * | 7/2004 | Chang et al. | 424/471 |
| 2005/0129778 A1 * | 6/2005 | Mulye | 424/490 |

FOREIGN PATENT DOCUMENTS

WO    WO 9961005 A1 * 12/1999

OTHER PUBLICATIONS

Physician's Desk Reference, 55th Edition (2001), pp. 606-607.

* cited by examiner

*Primary Examiner*—S. Tran

(57) ABSTRACT

The present invention relates to a controlled release pellet of metoprolol and its pharmaceutically acceptable salts that uses a water soluble or a water swellable inert starting seed or core.

37 Claims, No Drawings

FORMULATION AND PROCESS FOR DRUG LOADED CORES

FIELD OF THE INVENTION

The present invention relates to the field of oral pharmaceutical dosage forms with controlled release of an active ingredient from a drug core loaded with a high percentage of active ingredient. Specifically, the present invention relates to $beta_1$ adrenergic blocking agent pellets that are compressed into a tablet or loaded into a capsule shell, and a method of preparation of such pellets wherein the pellets are comprised of water soluble or water swellable inert starting seeds or cores. More specifically, the $beta_1$ adrenergic blocking agent is metoprolol.

BACKGROUND OF THE INVENTION

A constant time controlled and/or a pH specific release of the active component of an orally administered drug is advantageous in medical treatment. The present invention relates to the oral administration of doses of metoprolol and its pharmaceutically acceptable salts such as, but not limited to, succinate, fumerate or benzoate of racemic metoprolol and the benzoate or sorbate of the S-enantiomer of metoprolol as disclosed in U.S. Pat. No. 4,957,745, U.S. Pat. No. 5,001,161 and U.S. Pat. No. 5,081,154 and incorporated herein by reference. The therapeutic effect of these drugs can be seen in the normalization of blood pressure for hypertension sufferers, and in the reduction of oxygen requirements in cardiac tissues, which induces beneficial affects on both angina pectoris and myocardial infarction.

Previously, inert cores for preparing controlled release forms of metoprolol pellets have been limited to water insoluble materials, because the use of water soluble materials combined with metoprolol created a great amount of osmotic pressure causing the controlled release pellets to burst and dump the drug. See U.S. Pat. No. 4,927,640 which is incorporated herein by reference.

SUMMARY OF THE INVENTION

The present invention solves the problems associated with the use of a water-soluble and/or water swellable cores for metoprolol controlled release pellets. The controlled release pellets are prepared by coating a drug layer or layers onto a water soluble or water swellable inert starting seed or core then applying over the drug layer a polymeric coating that controls the release of the drug. Said pellets are then formed into an extended release tablet or capsule for oral administration.

The controlled release pellets of the present invention are comprised of:

a) a water soluble or water swellable inert core;
b) a drug layer comprising metoprolol or a pharmaceutically acceptable salt thereof applied to the inert core; and
c) a controlled release coating surrounding the drug layer.

The pellets can be mixed with conventional tabletting excipients and compressed into a tablet or loaded into a capsule for oral administration.

The present invention also relates to a method of producing the pellets or beads.

Additionally, the present invention relates to the formation of a tablet using the controlled release pellets with and without additional active release pellets. The active release pellets being formed in the same method as the controlled release pellets, but without the controlled release coating.

In a preferred embodiment of the present invention an aqueous solvent system is used instead of an organic solvent system to apply the drug layer to the inert core. This process is also more environmentally friendly due to the lack of conventional organic solvents such as methylene chloride.

DETAILED DESCRIPTION OF THE INVENTION

In the present invention, the inert core is a water soluble or water swellable core. The inert core must be of sufficient density and strength to enable it to undergo coating in a fluidized bed process. The inert cores of the present invention should have a diameter less than 30 mesh and preferably less than 40 mesh. In a preferred embodiment the inert cores should have a diameter ranging from about 30 to 200 mesh, preferably 40 to 120 mesh and most preferred 60 to 80 mesh.

Suitable water-soluble cores are sugar seeds or nonpareils that are well known in the art. Examples of water swellable cores are microcrystalline cellulose spheres commercially available from FMC Corporation under the trade name CELPHERE®.

The pharmaceutically active ingredient or drug that is applied to the inert core is metoprolol or its pharmaceutically acceptable salts, such as, succinate, fumarate, tartrate, citrate, pamoate, mandelate or others that are described in U.S. Pat. Nos. 4,281,654; 4,303,637; 4,957,745; 5,001,161 and 5,081,154 which are incorporated herein by reference. The metoprolol or its pharmaceutically acceptable salts may be in its racemic form or a pure enantiomer, such as, the s-enantiomer of the benzoate or sorbate salt. In one of the embodiments of the present invention it is preferred that the metoprolol used is micronized, so the average particle size is less than 100 microns, and preferably less than 50 microns, and most preferably not less than 25 microns.

In order for the drug to be applied to the inert core, a binding agent may be necessary. The binding agent employed in the active pellet can be any type of binding agent commonly known in the art. Examples of some of the preferred binding agents are polyvinyl pyrrolidone, hydroxyethyl cellulose, hydroxypropyl cellulose, hydroxypropyl methylcellulose, polyacrylate, ethylcellulose, or mixtures of the foregoing. In the preferred embodiment of the present invention, the binding agent is a water soluble or rapidly dispersible material, such as hydroxypropyl methylcellulose, or polyvinyl pyrrolidone.

The drug is applied to the inert core by any conventional techniques known in the industry, such as, pan coating, roto-granulation or fluidized bed coating. During such coating operations the drug is dispersed or dissolved in an organic or aqueous solvent, which may also contain other conventional excipients, such as the above mentioned binding agent. In a preferred embodiment, an aqueous solvent is employed. When the aqueous solvent is used, it may be necessary to include a surfactant in the solvent in order to keep the drug and other excipients suspended or dispersed.

If a surfactant is employed, it can be any type of surfactant commonly known in the art such as a fatty acid, a chelating agent, a bile salt or mixtures thereof. Examples of some preferred surfactants are fatty acids such as capric acid, oleic acid and their monoglycerides, especially alkyl sulfates, such as sodium lauryl sulfate, sodium dodecyl sulfate and polysorbate 80; chelating agents such as citric acid and phytic acid. The preferred surfactant used herein is polysorbate 80.

In a preferred embodiment of the present invention, the drug layer comprises the following ingredients:

TABLE I

| | Drug Layer | |
| Ingredients | Preferred | Most Preferred |
| --- | --- | --- |
| drug | 50-100% | 70-99% |
| binder | 0-50% | 1-25% |
| surfactant | 0-1.0% | 0-0.50% |

The above weight percentages are based on the total weight of the active coating layer.

Once the drug layer is applied to the inert core, a controlled release coat is applied to the drug layer. The controlled release coat is applied so that it prevents or retards the release of the drug from the pellet. The controlled release coat is preferably comprised of a polymeric film forming polymer and may optionally contain conventional processing aids such as emulsifiers, plasticizers, surfactants, lubricants or channeling agents.

The film forming polymers suitable for use in the controlled release coating are water insoluble polymers such as, ethylcellulose, cellulose acetate, cellulose propionate (lower, medium or higher molecular weight), cellulose acetate propionate, cellulose acetate butyrate, triacetate, cellulose acetate phathalate, cellulose tricetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene acrylate), poly(ethylene), poly(ethylene) low density, poly(ethylene) high density, poly(propylene), poly(ethylene terephthalate), poly(vinyl isobutyl ether), poly(vinyl acetate), poly(vinyl chloride), chitin, chitosan, poly(anhydrides), poly(lactic acid), ploy (glycolic acid), poly(ortho esters), poly(lactide co-glycollide), poly(hydroxy butyrate) or polyurethane or a mixture thereof.

As used herein the term water insoluble polymer includes polymers that are slightly permeable to water. A suitable polymer which is slightly permeable to water is a polymer sold under the trade name Eudragit® RS. Eudragit® Polymers are polymeric lacquer substances based on arcylates and methylarcylates.

The controlled release coating may be built up applying a plurality of coats of polymer solution or suspension to the drug core as hereinafter described. The membrane solution or suspension contains the polymer(s) dissolved or suspended, respectively, in a suitable aqueous or organic solvent or mixture of solvents, optionally in the presence of a conventional excipient.

The controlled release coating solution or suspension may be applied to the active cores in a conventional coating pan as indicated or, alternatively, using an automated system such as a CF granulator, for example a FREUND CF® granulator, a GLATT® fluidized bed processor, a modified ACCELA-COTA® or other suitably automated bead coating equipment.

Suitable emulsifiers that can be used in the present invention are may include, but are not limited to, phospholipids, polysorbate, propylene glycol, poloxamer, glyceryl monostearate, other pharmaceutical emulsifiers and/or mixtures thereof.

Suitable surfactants that may optionally be used in the present invention are sodium lauryl sulfate, sodium taurocholate or a polysorbate.

The controlled release coating may optionally include a plasticizing agent. Plasticizers are used to increase the resiliency of the finished product from cracking and fracturing. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil, poloxamers and varying percentages of acetylated monoglycerides.

Suitable lubricants possess anti-sticking or anti-tacking properties. Suitable lubricants used in preparing solid dosage forms may include talc, stearic acid, magnesium stearate, glyceryl monostearate, sodium stearyl fumerate, hydrogenated oils, polyethylene glycols and sodium stearate. A particularly preferred lubricant is talc.

A channeling agent is an excipient that is incorporated into the controlled release coating and functions to increase the volume of fluid imbibed into the core. It creates channels, preferably tortuous channels that enable gastric and intestinal fluid to enter the core and allow the active compound to leave the core. The channeling agent can be a water soluble material or an enteric material. Some examples of the preferred materials that are useful as channeling agents are sodium chloride, potassium chloride, sucrose, sorbitol, mannitol, polyethylene glycol (PEG), propylene glycol, hydroxypropyl cellulose, hydroxypropyl methycellulose, hydroxypropyl methycellulose phthalate, cellulose acetate phthalate, polyvinyl alcohols, cellulose acetate butyrate, methacrylic acid copolymers, zein and mixtures thereof. The preferred channeling agent is Eudragit® S100, a methacrylic acid copolymer commercially available from Rohm Pharma Gmbh.

The channeling agent may also be a water soluble drug. If the channeling agent is a drug, such as metoprolol, the present dosage form has the added advantage of providing an immediate release of active component.

In a preferred embodiment of the present invention, the controlled release coating comprises the following ingredients:

TABLE II

| | Extended Release Coating | |
| Ingredients | Preferred | Most Preferred |
| --- | --- | --- |
| water insoluble polymers | 50-95% | 75-90% |
| emulsifier | 0-25% | 5-15% |
| channeling agent | 0-15% | 2-10% |

The above weight percentages are based on the total weight of the newly formed extended release coating layer.

Once the controlled release coat is applied to the active cores, a plurality of the pellets may be compressed into a tablet or filled into a gelatin capsule, HPMCP capsule, HPMC capsule and/or pullulan capsule. The tablet forming processes preferably involves the mixing of the controlled release pellets with a disintegrant, a lubricant (or plasticizer) and a surfactant. The mixture is then compressed with a cushioning agent into a tablet and optionally coated with a color, esthetic or polishing coat. Suitable cushioning agents include, but are not limited to glyceryl monostearate, various grades of microcrystalline cellulose, lactose and mixtures thereof.

The controlled release pellets prepared in accordance with the present invention should exhibit the following dissolution profile when tested in a USP Type 2 apparatus, at 75 rpm, 37° C. and in a phosphate buffer medium with a pH of 7.5.

TABLE III

| Time | Preferred | Most Preferred |
|---|---|---|
| 2 hours | 0-40% | 0-25% |
| 4 hours | 5-50% | 10-45% |
| 8 hours | 25-80% | 35-75% |
| 16 hours | NLT 50% | NLT 75% |

NLT = not less than

Disintegrants used in the tabletting process are added to assist in the break down of the tablet. Suitable disintegrants are crospovidone XL-10, microcrystalline cellulose pH-102, microcrystalline cellulose pH-200, sodium starch glycolate and the like. The preferred disintegrant in the present invention is a mixture of crospovidone XL-10, microcrystalline cellulose pH-102 and microcrystalline cellulose pH-200.

Microcrystalline cellulose is added to improve the tabletting properties and assist in disintegration of the tablet in vitro. This in turn, assists in the release of the active pellets in the body. In a preferred embodiment, microcrystalline cellulose is used as a filler and cushioning agent. A cushioning agent is an excipient which facilitates compression of pellets into a tablet or capsule, and helps protect coated pellets from severe compaction forces and surface cracking.

Lubricants are used in the tabletting process to prevent the mixture of components from sticking to the equipment during the tabletting. The lubricant also aids the ejection of the tablet from the dies, and additionally may help improve powder flow. Suitable lubricants are described above. The preferred lubricant in this step of the present invention is glyceryl monostearate. Additionally, lubricants provide cushioning properties.

In a preferred embodiment of the present invention, the tablet comprises the following ingredients:

TABLE IV

| | Tabletting | |
|---|---|---|
| Ingredients | Preferred | Most Preferred |
| Controlled Release Pellets | 15-70% | 25-50% |
| Disintegrant/cushioning agent | 5-70% | 30-50% |
| Lubricant | 5-40% | 5-30% |

The above weight percentages are based on the total weight of the newly formed tablet.

If an immediate release dose of the active ingredients is desired for the final dosage form, the tablet or capsule may further comprise a therapeutically effective amount of the drug which can be mixed into the tablet excipient or with the controlled release pellets prior to encapsulation. In a preferred embodiment, the immediate release amount of the drug is provided by adding active drug pellets or pellets which have not been coated with the controlled release coating to the controlled release pellets prior to encapsulation or tabletting. In a more preferred embodiment of the present invention, a tablet will have the following composition:

TABLE V

| | TABLETTING | |
|---|---|---|
| Ingredients | Preferred | Most Preferred |
| Controlled Release Pellets | 15-60% | 25-45% |
| Active Pellets | 1-15% | 2-8% |
| Disintegrant/Cushioning Agent | 20-70% | 30-50% |
| Lubricant | 5-40% | 5-30% |

The above weight percentages are based on the total weight of the newly formed tablet, and the components are as described above.

A tablet or capsule containing the controlled release pellets prepared in accordance with the present invention and an immediate release form of metoprolol should exhibit the following dissolution profile when tested in a USP Type 2 apparatus at 75 rpm, 37° C. and in a phosphate buffer medium with a pH of 7.5

TABLE VI

| Time | Preferred | Most Preferred |
|---|---|---|
| 2 hours | 0-50% | 10-40% |
| 4 hours | 10-60% | 20-50% |
| 8 hours | 25-80% | 35-75% |
| 16 hours | NLT 50% | NLT 60% |

NLT = not less than

The tablet or capsule containing the controlled release pellets prepared in accordance with the present invention and containing an immediate release amount of the metoprolol should obtain its peak plasma level within about 3 to 8 hours, preferably about 4.5 hours to about 7.5 hours and have a $C_{max}$ of less than 300 ng/ml, preferably less than 275 ng/ml, and most preferably between 200 ng/ml and 275 ng/ml.

DESCRIPTION OF THE PREFERRED EMBODIMENT

The present invention will be further illustrated by the following examples

EXAMPLE I

A controlled release metoprolol succinate tablet in accordance with the present invention is prepared as follows.

Stage I Drug Layering Process 0.7378 kg of hydroxypropyl methylcellulose (Methocel E-5) is dissolved in 44.100 kg of purified water using a mechanical stirrer until a clear solution is obtained. 14.775 kg of metoprolol succinate and 0.0205 kg of Tween 80 are then added into the solution. Once the drug is added, the suspension should be constantly stirred until the spraying process is completed to avoid settling.

5.327 kg of sugar spheres NF 60/80 are placed into a fluidized bed coater. The product air temperature of the coater should be higher than 45° C. prior to loading the sugar spheres into the fluidized bed coater. The drug suspension prepared above is sprayed onto the sugar seeds using the following conditions:

TABLE VII

| | |
|---|---|
| Nozzle tip diameter | 1.2 mm |
| Screen Size | 100 mesh |
| Shaking interval | 30 min |
| Shaking Duration | 3 sec |
| Atomization Pressure | 2.5 bar |
| Inlet Air Temperature | 50-100° C. |
| Pump Rate | 5-80 mL/min |
| Tubing Size | 16 mm |

Once the drug suspension has been consumed the pellets are dried for 10 minutes or until the loss on drying (LOD) is less than 3%. Finally, the pellets are screened using 40 mesh and 80 mesh screens. The pellets between the 40 and 80 mesh are collected.

Pellets may be dusted with an anti-sticking agent which may include, but would not be limited to talc or silicon dioxide (commercially available as Aerosil®).

Stage II Polymer Coating Process for Metoprolol Succinate ER Pellets

A controlled release coating is prepared with the following composition:

TABLE VIII

| Metoprolol Active Pellets | Amount Per Batch (kg) |
|---|---|
| Cellulose Acetate Butyrate, PG CAB 171-15 | 2.0885 kg |
| Poloxamer 188 NF, Lutrol F-68 | 0.2500 kg |
| Eudragit ® S100 | 0.1488 kg |

The controlled release coating is prepared by dissolving 2.0885 kg of the cellulose acetate butyrate, 0.1488 kg of the Eudragit® S100, and 0.2500 kg of the Lutrol F-68 into a mixture of 5.500 kg of purified water and 49.00 kg of acetone and stirred until the solution is clear using a mechanical stirrer. The solution is then applied to active or drug layered pellets prepared above in Stage I using a bottom spray fluidized bed coater with the same parameters as described for the application of the drug layer in Stage I.

After the controlled release solution has been consumed the pellets are dried for 10 minutes or until the LOD is less than 3%. Finally, pellets are screened through 25 and 80 mesh screens and the pellets between the 25 and 80 mesh screens are collected.

Stage III Tabletting and Seal/Color Coating of Metoprolol Succinate ER Tabs

A tablet in accordance with the present invention is prepared with the following composition:

TABLE IX

| Ingredients | Amount per Batch (kg) |
|---|---|
| Metoprolol Succinate Controlled Release Pellets (Stage II) | 38.220 kg |
| Metoprolol Active Pellets (Stage I) | 4.998 kg |
| Microcrystalline Cellulose (Avicel PH-102) | 11.312 kg |
| Microcrystalline Cellulose (Avicel PH-200) | 26.320 kg |
| Crospovidone (XL-10), NF | 3.150 kg |
| Glyceryl Monostearate | 21.000 kg |

The microcrystalline cellulose, crospovidone, metoprolol controlled release pellets prepared in Stage II above, and metoprolol active pellets prepared in Stage I above are added to a blender and mixed for 15 minutes. The glyceryl monostearate is then added to the blender and blended for an additional 5 minutes. The resulting mixture is then compressed into tablets.

The resulting tablet should have a hardness between 5-25 kp, with a target of 15 kp.

The resulting tablet may optionally be seal coated using a seal coat solution and a binder. In the present invention the seal coat is formed using Opadry White and hydroxypropyl methylcellulose. The seal coat materials are dissolved in water and applied to tablets using layering techniques commonly known in the industry such as fluidized bed coating, rotor granulation or pan coating.

EXAMPLE II

A controlled release metoprolol tablet in accordance with the present invention is prepared as follows.

Stage I Drug Layering Process 0.7378 kg of hydroxypropyl methylcellulose (Methocel E-5) is dissolved in 44.100 kg of purified water using a mechanical stirrer until a clear solution is obtained. 14.775 kg of metoprolol succinate and 0.0205 kg of Tween 80 are then added into the solution. Once the drug is added, the suspension should be constantly stirred until the spraying process is completed to avoid settling.

5.327 kg of microcrystalline cellulose spheres, CELPHERE® CP-203, are placed into a fluidized bed coater. The product air temperature should be higher than 45° C. prior to loading the microcrystalline cellulose spheres into the fluidized bed coater. The drug suspension prepared above is sprayed onto the microcrystalline cellulose spheres using the parameters set forth in Example I.

Once the drug suspension has been consumed, the pellets are dried for 10 minutes or until the loss on drying (LOD) is less than 3%. Finally, the pellets are screened using 40 mesh and 80 mesh screens. The pellets between the 40 and 80 mesh screen are collected.

Stage II Polymer Coating Process for Metoprolol Succinate ER Pellets

A controlled release coating is prepared with the following composition:

TABLE X

| Metoprolol Active Pellets | Amount Per Batch (kg) |
|---|---|
| Cellulose Acetate Butyrate, PG CAB 171-15 | 2.0885 kg |
| Poloxamer 188 NF, Lutrol F-68 | 0.2500 kg |
| Eudragit ® S100 | 0.1488 kg |

The controlled release coating is prepared by dissolving 2.0885 kg of the cellulose acetate butyrate, 0.1488 kg of the Eudragit® S100, and 0.2500 kg of the Lutrol F-68 into a mixture of 5.500 kg of purified water and 49.00 kg of acetone and stirred until the solution is clear using a mechanical stirrer. The solution is then applied to the active or drug layered pellets prepared above in Stage I using a bottom spray fluidized bed coater with the same parameters as described for the application of the drug layer in Stage I.

After the controlled release solution has been consumed the pellets are dried for 10 minutes or until the LOD is less than 3%. Finally, pellets are screened through 25 and 80 mesh screens and the pellets between the 25 and 80 mesh screens are collected.

Stage III Tabletting and Seal/Color Coating of Metoprolol Succinate ER Tabs

A tablet in accordance with the present invention is prepared with the following composition.

TABLE XI

| Ingredients | Amount per Batch (kg) |
|---|---|
| Metoprolol Succinate Controlled Release Pellets (Stage II) | 38.220 kg |
| Metoprolol Active Pellets (Stage I) | 4.998 kg |
| Microcrystalline Cellulose (Avicel PH-102) | 11.312 kg |
| Microcrystalline Cellulose (Avicel PH-200) | 26.320 kg |
| Crospovidone (XL-10), NF | 3.150 kg |
| Glyceryl Monostearate | 21.000 kg |

The microcrystalline cellulose, crospovidone, metoprolol controlled release pellets prepared in Stage II above, metoprolol active pellets prepared in Stage I above are added to a blender and mixed for 15 minutes. The glyceryl monostearate is then added to the blender and blended for an additional 5 minutes. The resulting mixture is then compressed into tablets.

The resulting tablet should have a hardness between 5-25 kp, with a target of 15 kp.

The resulting tablet may optionally be seal coated using a seal coat solution and a binder. In the present invention the seal/color coat is formed using Opadry White and hydroxypropyl methylcellulose. The seal coat materials are dissolved in water and applied to tablets using layering techniques commonly known in the industry such as fluidized bed coating, rotor granulation or pan coating.

EXAMPLE III

A controlled release metoprolol succinate tablet in accordance with the present invention is prepared as follows.

Stage I First Drug Layering Process 0.4438 kg of hydroxypropyl methylcellulose (Methocel E-5) is dissolved in 26.500 kg of purified water using a mechanical stirrer until a clear solution is obtained. 8.8620 kg of metoprolol succinate and 0.0112 kg of Tween 80 are then added into the solution. Once the drug is added, the suspension should be constantly stirred until the spraying process is completed to avoid settling.

5.3270 kg of sugar spheres NF 60/80 are placed into a fluidized bed coater. The product air temperature should be higher than 45° C. prior to the loading of the sugar spheres into the fluidized bed coater. The drug suspension prepared above is sprayed onto the sugar spheres using the parameters set forth in Example I.

Once the drug suspension has been consumed, the pellets are dried for 10 minutes in the fluidized bed coater or until the loss on drying (LOD) is less than 3%.

Stage II Second Drug Layering Process 0.2940 kg of hydroxypropyl methylcellulose (Methocel E-5) is dissolved in 17.600 kg of purified water using a mechanical stirrer until a clear solution is obtained. 5.9130 kg of metoprolol succinate and 0.0093 kg of Tween 80 are then added into the solution. Once the drug is added to the suspension, it should be stirred continuously until the spraying process is completed to avoid settling.

14.644 kg of metoprolol active pellets from Stage I are placed into a fluidized bed coater. The product air temperature should be higher than 45° C. prior to loading the metoprolol active pellets into the fluidized bed coater. Begin spraying the drug suspension prepared in Stage II above using the parameters set forth in Example I.

Once the drug suspension has been consumed the pellets are dried for 10 minutes or until the loss on drying (LOD) is less than 3%. Finally, the pellets are screened using 40 mesh and 80 mesh screens. The pellets between the 40 and 80 mesh are collected.

Stage III Polymer Coating Process for Metoprolol Succinate ER Pellets

A controlled release coating is prepared with the following composition:

TABLE XII

| Metoprolol Active Pellets | Amount Per Batch (kg) |
|---|---|
| Cellulose Acetate Butyrate, PG CAB 171-15 | 2.0885 kg |
| Poloxamer 188 NF, Lutrol F-68 | 0.2500 kg |
| Eudragit ® S100 | 0.1488 kg |

The controlled release coating is prepared by dissolving 2.0885 kg of the cellulose acetate butyrate, 0.1488 kg of the Eudragit® S100, and 0.2500 kg of the Lutrol F-68 into a mixture of 5.500 kg of purified water and 49.00 kg of acetone and stirred until the solution is clear using a mechanical stirrer. The solution is then applied to active or drug layered pellets prepared above in Stage II using the bottom spray fluidized bed coater with the same parameters as described for the application of the drug layer in Stage I.

After the controlled release solution has been consumed the pellets are dried for 10 minutes or until the LOD is less than 3%. Finally, pellets are screened through 25 and 80 mesh screens and the pellets between the 25 and 80 mesh screens are collected.

Stage IV Tabletting and Seal/Color Coating of Metoprolol Succinate ER Tabs

A tablet in accordance with the present invention is prepared with the following composition:

TABLE XIII

| Ingredients | Amount per Batch (kg) |
|---|---|
| Metoprolol Succinate Controlled Release Pellets (Stage III) | 38.220 kg |
| Metoprolol Active Pellets (Stage I) | 4.998 kg |
| Microcrystalline Cellulose (Avicel PH-102) | 11.312 kg |
| Microcrystalline Cellulose (Avicel PH-200) | 26.320 kg |
| Crospovidone (XL-10), NF | 3.150 kg |
| Glyceryl Monostearate | 21.000 kg |

The microcrystalline cellulose, crospovidone, metoprolol controlled release pellets prepared in Stage III above, and metoprolol active pellets prepared in Stage II above are added to a blender and mixed for 15 minutes. The glyceryl monostearate is then added to the blender and blended for an additional 5 minutes. The resulting mixture is then compressed into tablets.

The resulting tablet should have a hardness between 5-25 kp, with a target of 15 kp.

The resulting tablet may optionally be seal coated using a seal/color coat solution and a binder. In the present invention the seal coat is formed using Opadry White and hydroxypropyl methylcellulose. The seal coat materials are dissolved in water or alcohol and applied to tablets using layering techniques commonly known in the industry such as fluidized bed coating, rotor granulation or pan coating.

EXAMPLE IV

A controlled release metoprolol tablet in accordance with the present invention is prepared as follows.

Stage I Drug Layering Process 0.810 kg of hydroxypropyl methylcellulose (Methocel E-5) is dissolved in 48.800 kg of purified water using a mechanical stirrer until a clear solution is obtained. 16.200 kg of metoprolol succinate and 0.0210 kg of Tween 80 are then added into the solution. Once the drug is added, the suspension should be constantly stirred until the spraying process is completed to avoid settling.

6.849 kg of sugar spheres, are placed into a fluidized bed coater. The product air temperature should be higher than 45° C. prior to loading the microcrystalline cellulose spheres into the fluidized bed coater. The drug suspension prepared above is sprayed onto the sugar spheres using the parameters set forth in Example I.

Once the drug suspension has been consumed, the pellets are dried for 10 minutes or until the loss on drying (LOD) is less than 3%. Finally, the pellets are screened using 40 mesh and 80 mesh screens. The pellets between the 40 and 80 mesh screen are collected.

Stage II Polymer Coating Process for Metoprolol Succinate ER Pellets

A controlled release coating is prepared with the following composition:

TABLE XIV

| Metoprolol Active Pellets | Amount Per Batch (kg) |
|---|---|
| Cellulose Acetate Butyrate, PG CAB 171-15 | 2.992 kg |
| Poloxamer 188 NF, Lutrol F-68 | 0.3564 kg |
| Eudragit ® S100 | 0.2138 kg |

The controlled release coating is prepared by dissolving 2.992 kg of the cellulose acetate butyrate, 0.2138 kg of the Eudragit® S100, and 0.3564 kg of the Lutrol F-68 into a mixture of 7.125 kg of purified water and 64.12 kg of acetone and stirred until the solution is clear using a mechanical stirrer. The solution is then applied to active or drug layered pellets prepared above in Stage I using a bottom spray fluidized bed coater with the same parameters as described for the application of the drug layer in Stage I.

After the controlled release solution has been consumed the pellets are dried for 10 minutes or until the LOD is less than 3%. Finally, pellets are screened through 40 and 80 mesh screens and the pellets between the 40 and 80 mesh screens are collected.

Stage III Tabletting and Seal/Color Coating of Metoprolol Succinate ER Tabs

A tablet in accordance with the present invention is prepared with the following composition.

TABLE XV

| Ingredients | Amount per Batch (kg) |
|---|---|
| Metoprolol Succinate Controlled Release Pellets (Stage II) | 47.498 kg |
| Metoprolol Active Pellets (Stage I) | 3.856 kg |
| Microcrystalline Cellulose (Avicel PH-102) | 38.961 kg |
| Microcrystalline Cellulose (Avicel PH-200) | 38.961 kg |
| Crospovidone (XL-10), NF | 4.374 kg |
| Glyceryl Monostearate | 12.150 kg |

The microcrystalline cellulose, crospovidone, metoprolol controlled release pellets prepared in Stage II above, metoprolol active pellets prepared in Stage I above are added to a blender and mixed for 15 minutes. The glyceryl monostearate is then added to the blender and blended for an additional 5 minutes. The resulting mixture is then compressed into tablets.

The resulting tablet should have a hardness between 5-25 kp, with a target of 15 kp.

The resulting tablet may optionally be seal coated using a seal coat solution and a binder. In the present invention the seal coat is formed using Opadry White and hydroxypropyl methylcellulose. The seal/color coat materials are dissolved in water and applied to tablets using layering techniques commonly known in the industry such as fluidized bed coating, rotor granulation or pan coating.

EXAMPLE V

A controlled release metoprolol tablet in accordance with the present invention and possessing the following ingredients in mg/unit is prepared as follows:

Stage I Drug Layering Process

A metoprolol active pellet is prepared comprising 38.05 mg/unit of a 60/80 mesh sugar sphere layered with a drug layer comprising 9.5 mg/unit of hydroxypropyl methylcellulose (Methocel E-5), 190 mg/unit metoprolol succinate and 0.25/unit mg of Tween 80. The drug layer is applied to the sugar sphere from an aqueous suspension of the drug layer ingredients using a fluidized bed coater.

Stage II Polymer Coating Process for Metoprolol Succinate ER Pellets

A controlled release coating is applied to 237.8 mg/unit of metoprolol active pellets, said coating comprising 75.77 mg/unit cellulose acetate butyrate (PG CAB 171-15); 9.02 mg/unit of Poloxamer 188 NF, (Lutrol F-68); and 5.41 mg/unit of methacrylic acid copolymer (Eudragit® S-100). The controlled release coating ingredients are dissolved in an water acetone mixture and applied to the active pellets using a fluidized bed coater.

Stage III Tabletting and Seal/Color Coating of Metoprolol Succinate ER Tabs

A tablet is then formed comprising 295.2 mg/unit metoprolol ER pellets, 23.78 mg/unit metoprolol active pellets, 239.51 mg/unit microcrystalline cellulose (Avicel PH-102), 239.51 mg/unit microcrystalline cellulose (Avicel PH-200), 75 mg/unit glyceryl monostearate 600 P (and/or Myverol 18-06 PK) and 27 mg/unit Crospovidone (XL-10).

The resulting tablet may optionally be seal coated using a seal/color coat solution and a binder. In the present invention the seal coat is formed using 20 mg/unit of Opadry White and 5 mg/unit of Opadry Clear.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pellet consisting essentially of:
   a) an inert core that is water swellable;
   b) a drug layer applied to the inert core comprising:
      i) metoprolol succinate;
      ii) a binder; and
      iii) optionally a surfactant;
   c) a controlled release coating surrounding the drug layer comprising:
      i) 75-90% of a water insoluble film forming polymer selected from the group consisting of cellulose acetate, cellulose acetate butyrate, ethyl cellulose, hydroxypropyl cellulose acetate, hydroxypropyl methyl phthalate and cellulose acetate phthalate or mixtures thereof.

2. A controlled release pellet as defined in claim 1, wherein the inert core has a diameter that is less than 30 mesh.

3. A controlled release pellet as defined in claim 1, wherein the inert core has a diameter that is less than 40 mesh.

4. A controlled release pellet as defined in claim 1, wherein the inert core has a diameter of about 30 to 200 mesh.

5. A controlled release pellet as defined in claim 1, wherein the inert core has a diameter of about 40 to 120 mesh.

6. A controlled release pellet as defined in claim 1, wherein the inert core has a diameter of about 60 to 80 mesh.

7. The controlled release pellet as defined in claim 1, wherein the binder is selected from the group consisting of polyvinyl pyrrolidone, hydroxyethyl cellulose, hydroxypropyl cellulose, hydroxypropyl methylcellulose, polyacrylate, ethylcellulose, or mixtures of the thereof.

8. The controlled release pellet as defined in claim 7, wherein the binder is hydroxypropyl methylcellulose.

9. The controlled release pellet as defined in claim 1, wherein the drug layer further comprises a surfactant.

10. The controlled release pellet as defined in claim 9, wherein the surfactant is selected from the group consisting of fatty acids, chelating agents, bile salts or mixtures thereof; capric acid, oleic acid and their monoglycerides, alkyl sulfates, sodium lauryl sulfate, sodium dodecyl sulfate, polysorbate 80, citric acid and phytic acid.

11. The controlled release pellet as defined in claim 10, wherein the surfactant is polysorbate 80.

12. The controlled release pellet as defined in claim 1, wherein the water insoluble film-forming polymer is cellulose acetate butyrate.

13. The controlled release pellet as defined in claim 1, wherein the emulsifier is selected from the group consisting of phospholipids, propylene glycol, polysorbates, poloxamer, glyceryl monostearate, other pharmaceutical emulsifiers or mixtures thereof.

14. The controlled release pellet as defined in claim 1, wherein the emulsifier is a poloxamer.

15. The controlled release pellet as defined in claim 1, wherein the controlled release coating further comprises a plasticizer.

16. The controlled release pellet as defined in claim 15, wherein the plasticizer is selected from the group consisting of polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil, poloxamer and varying percentages of acetylated monoglycerides.

17. The controlled release pellet defined in claim 1 that exhibits the following dissolution profile when tested in a USP Type 2 apparatus at 75 rpm and 37° C. in a phosphate buffer with a pH of 7.5,
   0-25% of the metoprolol is released after 2 hours;
   10-45% of the metoprolol is released after 4 hours;
   35-75% of the metoprolol is released after 8 hours;
   not less than 75% of the metoprolol is released after 16 hours.

18. An oral pharmaceutical tablet that comprises the controlled release pellet as defined in claim 1.

19. An oral pharmaceutical capsule that comprises the controlled release pellet as defined in claim 1.

20. The oral pharmaceutical tablet that is defined in claim 18 that further comprises an immediate release form of metoprolol.

21. The oral pharmaceutical capsule that is defined in claim 19 that further comprises an immediate release form of metoprolol.

22. The oral pharmaceutical tablet as defined in claim 20 that exhibits the following dissolution profile when tested in a USP Type 2 apparatus at 75 rpm and 37° C. in a phosphate buffer with a pH of 7.5,
   0-50% of the metoprolol is released after 2 hours;
   10-60% of the metoprolol is released after 4 hours;
   25-80% of the metoprolol is released after 8 hours;
   not less than 50% of the metoprolol is released after 16 hours.

23. The oral pharmaceutical tablet as defined in claim 22 that exhibits the following dissolution profile when tested in a USP Type 2 apparatus at 75 rpm and 37° C. in a phosphate buffer with a pH of 7.5,
   10-40% of the metoprolol is released after 2 hours;
   20-50% of the metoprolol is released after 4 hours;
   35-75% of the metoprolol is released after 8 hours;
   not less than 60% of the metoprolol is released after 16 hours.

24. The oral pharmaceutical capsule as defined in claim 21 that exhibits the following dissolution profile when tested in a USP Type 2 apparatus at 75 rpm and 37° C. in a phosphate buffer with a pH of 7.5,
   0-50% of the metoprolol is released after 2 hours;
   10-60% of the metoprolol is released after 4 hours;
   25-80% of the metoprolol is released after 8 hours;
   not less than 50% of the metoprolol is released after 16 hours.

25. The oral pharmaceutical capsule as defined in claim 24 that exhibits the following dissolution profile when tested in a USP Type 2 apparatus at 75 rpm and 37° C. in a phosphate buffer with a pH of 7.5,
   10-40% of the metoprolol is released after 2 hours;
   20-50% of the metoprolol is released after 4 hours;
   35-75% of the metoprolol is released after 8 hours;
   not less than 60% of the metoprolol is released after 16 hours.

26. The pharmaceutical tablet as defined in claim 20 that exhibits a peak plasma level between 3 and 8 hours after administration.

27. The pharmaceutical tablet as defined in claim 26 that exhibits a peak plasma level between about 4.5 hours to about 7.5 hours after administration.

28. The pharmaceutical capsule as defined in claim 21 that exhibits a peak plasma level between 3 and 8 hours after administration.

29. The pharmaceutical capsule as defined in claim 28 that exhibits a peak plasma level between about 4.5 hours to about 7.5 hours after administration.

30. The pharmaceutical tablet as defined in claim 20 that exhibits a $C_{max}$ of less than 300 ng/ml.

31. The pharmaceutical tablet as defined in claim 30 that exhibits a $C_{max}$ of less than 275 ng/ml.

32. The pharmaceutical tablet as defined in claim 31 that exhibits a $C_{max}$ of between 200 ng/ml and 275 ng/ml.

33. The pharmaceutical capsule as defined in claim 21 that exhibits a $C_{max}$ of less than 300 ng/ml.

34. The pharmaceutical capsule as defined in claim 33 that exhibits a $C_{max}$ of less than 275 ng/ml.

35. The pharmaceutical capsule as defined in claim 34 that exhibits a $C_{max}$ of between 200 ng/ml and 275 ng/ml.

36. A controlled release pellet as defined in claim 1, wherein the inert core is microcrystalline cellulose.

37. A process for preparing a controlled release pellet consisting essentially of:
   a) dissolving or suspending metoprolol succinate in an aqueous medium;
   b) applying the aqueous medium with the dissolved or suspended metoprolol succinate onto a water swellable inert core to create a drug layer on the inert core; and
   c) applying a controlled release coating to the drug layer, wherein the controlled release coating layer comprises:
      i) 75-90% of a water insoluble film forming polymer selected from the group consisting of cellulose acetate, cellulose acetate butyrate, ethyl cellulose, hydroxypropyl cellulose acetate, hydroxypropyl methyl phthalate and cellulose acetate phthalate or mixtures thereof;
      ii) 2-10% of a channeling agent comprising methacrylic acid copolymer; and
      iii) 5-15% of an emulsifier;

and wherein said pellet exhibits the following dissolution profile when tested in a USP Type 2 apparatus at 75 rpm and 37° C. in a phosphate buffer with a pH of 7.5;

0-40% of the metoprolol succinate is released after 2 hours;

5-50% of the metoprolol succinate is released after 4 hours;

25-80% of the metoprolol succinate is released after 8 hours;

not less than 50% of the metoprolol succinate is released after 16 hours.

* * * * *